United States Patent
Van Der Mark et al.

(10) Patent No.: US 6,480,281 B1
(45) Date of Patent: Nov. 12, 2002

(54) DEVICE FOR LOCALIZING AN OBJECT IN A TURBID MEDIUM

(75) Inventors: Martinus B. Van Der Mark, Eindhoven (NL); Gert W. 'T Hooft, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/527,200

(22) Filed: Mar. 16, 2000

(30) Foreign Application Priority Data

Mar. 23, 1999 (EP) .............................. 99200886

(51) Int. Cl.⁷ .............................................. G01N 21/49
(52) U.S. Cl. ...................... 356/432; 356/440; 356/344; 600/476
(58) Field of Search ............................... 356/432, 244, 356/440; 600/476

(56) References Cited

U.S. PATENT DOCUMENTS

| | | | |
|---|---|---|---|
| 4,347,850 A | * | 9/1982 | Kelly-Fry et al. .......... 600/437 |
| 5,907,406 A | * | 5/1999 | Papaioannou et al. ...... 356/432 |
| 6,064,073 A | * | 5/2000 | Hoogenraad ................ 250/573 |

FOREIGN PATENT DOCUMENTS

| | | | |
|---|---|---|---|
| WO | 8801151 | 2/1988 | ............. A61B/8/08 |
| WO | 9620638 | 7/1996 | ............. A61B/5/00 |
| WO | WO9903394 | 1/1999 | |

* cited by examiner

Primary Examiner—Richard A. Rosenberger
(74) Attorney, Agent, or Firm—John Vodopia

(57) ABSTRACT

The invention relates to a device for localizing objects in turbid media. The device can be used for optical mammography. In optical mammography the interior of the part of the breast to be examined is imaged. The device includes a holder for receiving the part of the breast of a female. This holder is provided with light sources and photodetectors. The holder also contains a matching liquid in order to provide an optical coupling between the light sources and the part of the breast and as well as an optical coupling between the part of the breast and the photodetectors. In order to obtain such images, the part of the breast of a female to be examined is positioned in the holder and a resilient sealing ring is placed around the part of the breast and the upper side of the holder. The resilient sealing ring improves the filling of the holder with matching liquid, thus reducing imaging artefacts in the reconstructed images.

18 Claims, 3 Drawing Sheets

DEVICE FOR LOCALIZING AN OBJECT IN A TURBID MEDIUM

BACKGROUND OF THE INVENTION

1. Field of the Invention

The invention relates to a device for imaging the interior of a turbid medium, which device includes a holder which has an open side bounded by an edge portion, encloses a measuring volume and is arranged to receive a matching liquid and the turbid medium, a light source for irradiating the turbid medium and the matching liquid, a photodetector for measuring a part of the light transported through the turbid medium and the matching liquid, and a control unit for reconstructing an image of the interior of the turbid medium on the basis of the measured intensities.

2. Description of Related Art

In the context of the present patent application the term light is to be understood to mean electromagnetic radiation of a wavelength in the range of from 400 to 1400 nm. Furthermore, a turbid medium is to be understood to mean a substance consisting of a material having a high light scattering coefficient. Examples in this respect are an Intralipid solution or biological tissue. Furthermore, an attenuation coefficient is to be understood to mean the inverse diffuse absorption distance κ which is given by $\kappa=\sqrt{3\mu_a\mu'_s}$, where $\mu'_s$ represents the reduced scattering coefficient and $\mu_a$ represents the absorption coefficient.

A device of the kind set forth is known from the patent application WO 99/03394. Such a device could be used for in vivo examinations for detecting the presence of any tumors in breast tissue of a human or animal female. To this end, the turbid medium, in this case being, for example, a part of the breast of the female to be examined, is immersed in the matching liquid in the holder. The holder also includes a first number of light sources and a second number of photodetectors which are distributed across the wall of the holder. The matching liquid provides optical coupling between the part of the breast to be imaged and the light sources and the photodetectors, respectively, in the holder. Furthermore, the optical parameters of the matching liquid, such as the reduced scattering coefficient $\mu'_s$ and the absorption coefficient $\mu_a$, are approximately equal to those of the part of the breast to be imaged. Furthermore, the matching liquid prevents optical short-circuiting between the light sources and the photodetectors. In the context of the present patent application an optical short-circuit is to be understood to mean a light path between one of the light sources and one of the photodetectors in the holder which does not extend through the part of the breast in the holder. Finally, the matching liquid counteracts boundary effects in the reconstructed image; such effects are caused by the difference in optical contrast between the interior of the breast tissue and the remaining space in the holder. In order to measure the intensities, alternately one of the light sources irradiates the part of the breast to be imaged and the photodetectors measure a part of the light transported through the part of the breast to be imaged. These measurements are repeated until the part to be imaged has been irradiated by all light sources present in the holder. The results of the measurements are stored in a memory of the control unit. The control unit subsequently reconstructs the image of the interior of the part of the breast to be imaged from the measured intensity measurements.

It is a drawback of the known device that artefacts, for example contrast spots, are liable to occur in the reconstructed image of the part of the breast to be imaged. As a result, it is impossible to observe contrast differences which are possibly caused by the presence of a tumor which is small in comparison with such a contrast spot. The image may also provide a false indication of a tumor in the part of the breast where no tumor is found after other diagnostic examinations.

Citation of a reference herein, or throughout this specification, is not to be construed as an admission that such reference is prior art to the Applicant's invention of the invention subsequently claimed.

SUMMARY OF THE INVENTION

It is an object of the device according to the invention to counteract the occurrence of said artefacts in the reconstructed image. To this end, the device according to the invention is characterized in that it is provided with an elastically deformable sealing ring which is provided on the edge portion of the holder. The invention is based on the recognition of the fact that one possible cause of said artefacts resides in the fact that the part of the turbid medium to be imaged often is not completely immersed in the matching liquid. Air is trapped in locations in the holder which do not contain matching liquid and in which the turbid medium does not directly contact the holder. Consequently, the desired optical coupling is not realized between the light sources and the part of the turbid medium to be imaged and/or between the part of the turbid medium to be imaged and the photodetectors. For example, when the turbid medium is a breast of a female to be examined, it occurs that the dimensions of the part of the breast to be imaged are smaller than the part to be imaged of an average breast for which the fixed holder has been designed, so that a large free space is liable to occur to the left or to the right of the breast in the fixed holder. This also gives rise to a large boundary with air present outside the holder, near the upper openings of the photodetectors. A further possibility is that the positioning of the breast in the holder removes matching liquid from the holder so that an air gap is formed or an air bubble is trapped. Furthermore, it may be that during the measurement a small amount of matching liquid is transported out of the holder due to motion of the body to be examined. By providing the elastically deformable sealing ring on the edge portion of the holder, the holder can be made to adjoin exactly the surface around the breast of the body to be examined. The elastically deformable sealing ring thus counteracts the escape of the liquid from the holder. It is a further advantage of the sealing ring that the level of the matching liquid can be increased so that the distance between the photodetectors near the edge portion in the holder and the surface of the matching liquid is increased. It is a further advantage that respiratory effects are precluded. As a result of the described advantages, said artefacts are reduced and the reproducibility of the reconstructed images is enhanced so that they are better suited for diagnostic purposes. That is, as the artefacts are reduced, the diagnostic quality is improved.

A special embodiment of the device according to the invention is characterized in that the sealing ring contains polyurethane (PUR) of a density in a range of from 0.01 to 0.4 kg/l. PUR is a material allowing economical manufacture of the sealing ring in large numbers. For this density the PUR has properties such that the sealing ring can be almost completely compressed under the weight of the body to be examined.

A further embodiment of the device according to the invention is characterized in that the sealing ring contains an internal chamber which extends along at least a part of the circumference of the sealing ring.

A further embodiment of the device according to the invention is characterized in that the internal chamber contains a gas. The elasticity of the sealing ring can be adapted to the weight of the body to be examined by filling the internal chamber with a gas or a mixture of gases, for example air.

A further embodiment of the device according to the invention is characterized in that the internal chamber is connected to a rigid pressure vessel. The sealing ring is connected to the rigid pressure vessel, for example via a tube. The rigid pressure vessel acts as a buffer volume, so that the pressure in the chamber of the sealing ring remains approximately constant even when the sealing ring is compressed. The pressure in the pressure vessel is then, for example 100 hPa higher than the atmospheric pressure.

A further embodiment of the device according to the invention is characterized in that the sealing ring is made of a material containing latex or silicon.

Another embodiment of the device according to the invention is characterized in that a diffuse reflector is provided on a side of the sealing ring which faces the measuring volume of the holder. A high diffusion reflection is advantageous in counteracting artefacts in the reconstructed image. The diffuse reflector can be provided, for example by coating the sealing ring with a lacquer on a titanium dioxide base.

A further embodiment of the device according to the invention is characterized in that the sealing ring is provided with an adapter ring for attaching the sealing ring to the edge portion of the holder.

A further embodiment yet of the device according to the invention is characterized in that the device includes a reservoir for storing matching liquid and a pump which is connected between the reservoir and the holder in order to adjust the level of the matching liquid to be received by the holder. An escaped quantity of liquid can be replenished by supplying matching liquid by means of the pump. The quantity of matching liquid pumped into the holder amounts to, for example 100 ml/minute.

The invention also relates to a sealing ring for use in said device.

BRIEF DESCRIPTION OF THE DRAWING

The above and other, more detailed aspects of the invention are apparent from and will be elucidated, by way of example, with reference to the drawing.

In the drawing.

DETAILED DESCRIPTION OF THE PREFERRED EMBODIMENT

Figure 1:
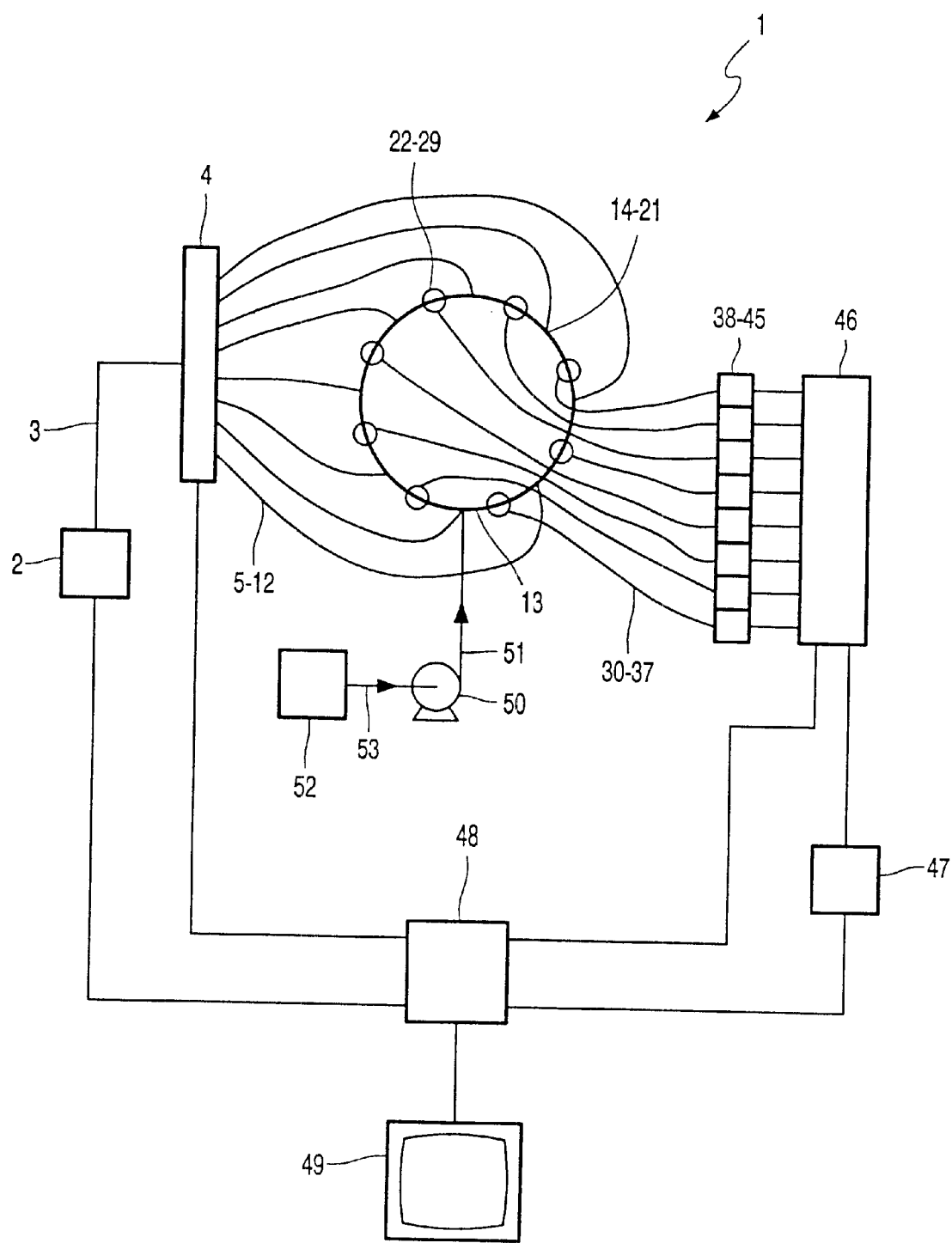
FIG. 1 shows a device for performing measurements on a part of the breast to be imaged.

FIG. 1 shows an embodiment of an optical mammography device 1 which is known per se. Even though the device is described, by way of example, as a mammography device, it can also be used for the examination of other parts of a human or animal body. The device described herein is intended for the localization of inhomogeneities in in vivo breast tissue of a part of a breast of a human body. A malignant tumor is an example of such an inhomogeneity. The device according to the invention is arranged to image such anomalies when they are still very small, so that a carcinoma can be detected at an early stage. However, such detection takes place without exposing the patient to the risks of examination by means of ionizing radiation, for example X-rays.

The device 1 includes a first plurality of N measuring light sources 14–21, a second plurality of M photodetectors 38–45, and a holder 13. The measuring light sources are mounted in the wall of the holder 13 in positions $r_i$, where i=1 ... N. The M photodetectors 38–45 are optically coupled to photodetector openings 22–29 in positions $r_j$ in the holder 13, where j=1 ... M. The numbers N and M are fixed and are valued, for example between 64 and 256. In practice these numbers equal 256 for N as well as M. In FIG. 1 the number of measuring light sources 14–21 and the number of photodetector openings 22–29 are chosen to be equal to eight for the sake of simplicity. The device 1 also includes a light source 2, a first optical light conductor 3, a multiple optical switch 4 and a plurality of optical conductors 512–12. The multiple optical switch 4 connects the light source 1, via the first optical conductor 3 and a second optical conductor, to one of the light-transmitting openings 14–21 in the wall of the holder 13, said openings constituting the measuring light sources. The light source 2 used is, for example a semiconductor laser with a wavelength of 810 nm. The measuring device 1 also includes a third plurality of optical conductors 30–37, a selection unit 46, an analog-to-digital converter 47, and a control device 48. The third optical conductors 30–37 are connected, via photodetector openings 22–29 in the wall of the holder 13, to the corresponding number of photodetectors 38–45. The exits of the photodetectors 38–45 are connected, via the selection unit 46, to the analog-to-digital converter 47. The output of the analog-to-digital converter is connected to an input of the control unit 48, for example a microcomputer.

The holder 13 is arranged to receive the part of the breast to be imaged and also a matching liquid. In order to perform intensity measurements wherefrom an image of the interior of a part of a breast of a female to be examined is reconstructed, the part of the breast of the female to be examined is immersed in matching liquid in the holder. The matching liquid serves inter alia to couple the light from the measuring light sources into the breast tissue. An example of a matching liquid is an Intralipid solution whose attenuation coefficient $\kappa_1$ corresponds to a predetermined mean attenuation coefficient of the breast tissue. The control unit 48 subsequently performs intensity measurements for each measuring light source/photodetector pair (i,j), where i=1 ... 256 and j=1 ... 256. The measured intensities are stored in a memory of the control unit 48. The control unit 48 subsequently reconstructs an image of the interior of the part of the breast of the female to be examined. A monitor 49 subsequently displays the reconstructed image. An example of an iterative method for reconstructing an image of the interior of the part of the breast to be examined is known from the cited patent application WO 99/03394.

The positioning of the part of the breast to be imaged in the holder and the fitting of the elastic sealing ring on the edge portion at the open side of the holder will be described in detail hereinafter with reference to FIG. 2.

Figure 2:
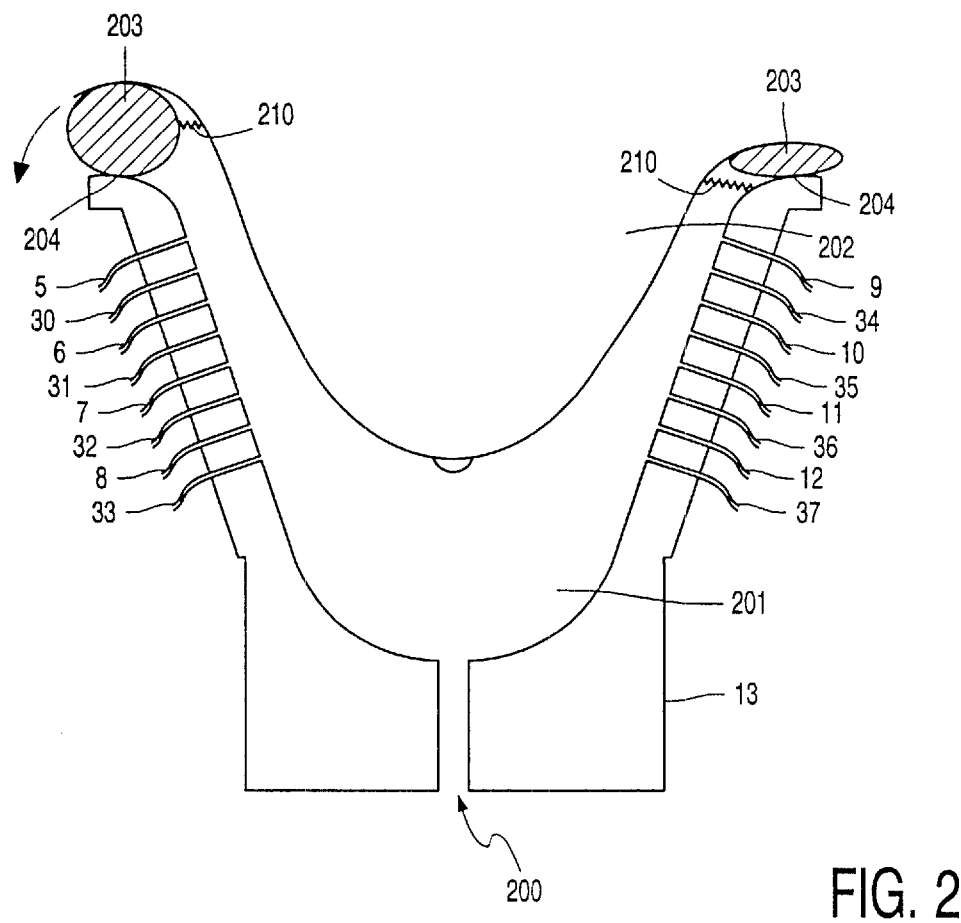
FIG. 2 is a sectional view of the holder containing the matching liquid and a part of the breast to be imaged.

FIG. 2 is a sectional view of the holder 13 and the part 202 of the breast of the female to be examined which is to be accommodated therein, and also a sectional view of a first embodiment 203 of the sealing ring. FIG. 2 also shows the optical conductors 5–12, 30–37, the matching liquid 201, and a connection 200 for a liquid pump. The first embodiment 203 of the sealing ring is arranged on an edge portion 204 at the open side of the holder 13 so that the sealing ring seals the part 202 of the breast to be imaged and the matching liquid 201 in the holder 13. The first embodiment 203 of the sealing ring is made of an elastic material, for example polyurethane foam of a density in a range of from 0.01 to 0.4 kg/l. For example, the density is 0.3 kg/l. Another feasible elastic material is, for example polyether. The first embodiment 203 of the sealing ring thus has elastic properties such that it can be compressed substantially completely under the weight of the body to be examined. Furthermore, the first embodiment 203 of the sealing ring is preferably shaped as a saddle, the diameter of the first embodiment of the sealing ring in the no-load state being different in two different locations along a symmetry axis of the sealing ring. This difference amounts to, for example 10 mm. During the positioning in the holder 13 of the part 202 of the breast of the female to be imaged, the first embodiment 203 of the sealing ring is arranged on the holder in such a manner that the part of the first embodiment 203 of the sealing ring which has the smallest diameter points in the direction of the feet of the female to be examined.

Figure 3:
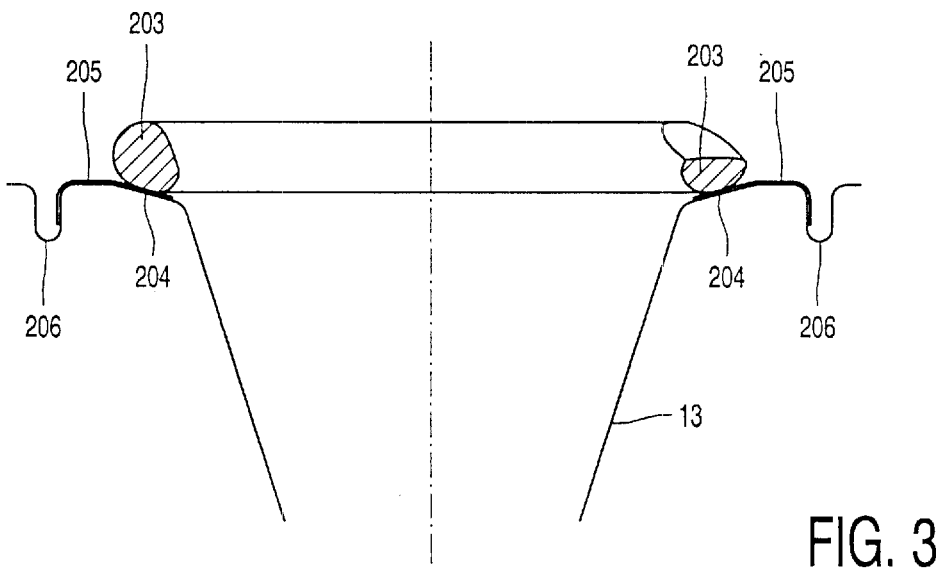
FIG. 3 is a sectional view of the first embodiment of the sealing ring provided with an adapter ring.

The first embodiment 203 of the sealing ring is attached, in a preferably watertight manner, to the edge portion 204 at the open side of the holder 13. Furthermore, in order to facilitate replacement of the first embodiment 203 of the sealing ring, it is preferably provided with an adapter ring. FIG. 3 shows an example of a first sealing ring with an adapter ring.

FIG. 3 is a sectional view of the holder 13 with the edge portion 204, a first sealing ring 203 and an adapter ring 205. FIG. 3 also shows a duct 206 which is provided in the edge portion 204 of the holder 14 and via which escaped matching liquid can be conducted, for example, to the reservoir 52 (shown in FIG. 1). The adapter ring 205 can be made of, for example PVC or polypropylene, for example by deep drawing. The thickness of the sheet material is in a range of from 0.1 mm to 0.4 mm and amounts to, for example 0.25 mm.

Figure 4:
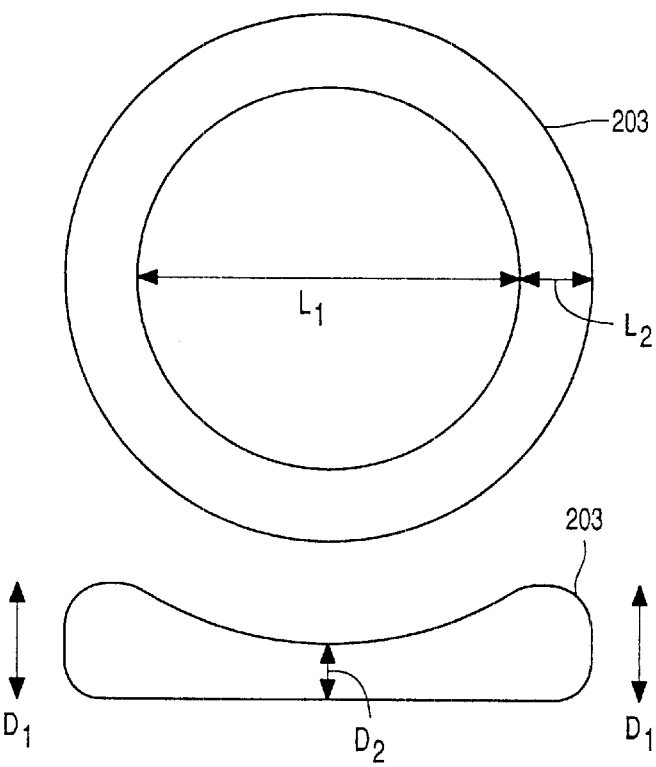
FIG. 4 is a plan view of the first embodiment of the sealing ring.

FIG. 4 is a first sectional view of a saddle-shaped first embodiment 203 of the sealing ring. The diameter L1 of the inner side of the sealing ring amounts to, for example 130 mm. The diameter distance in the direction of the L2 of the sealing ring amounts to, for example 20 mm.

Figure 5:
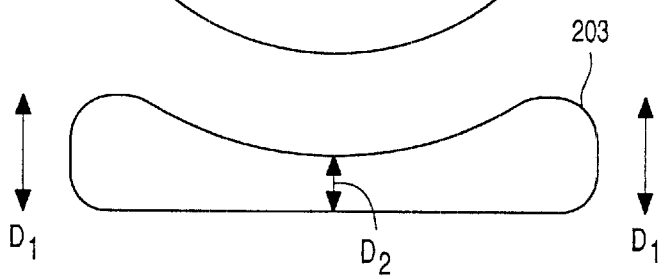
FIG. 5 is a side elevation of the first embodiment of the sealing ring.

FIG. 5 is a side elevation of a saddle-shaped first embodiment 203 of the sealing ring. In the no-load condition the largest thickness D1 of the first embodiment of the sealing ring amounts to, for example 30 mm and the smallest thickness D2 of the first embodiment of the sealing ring amounts to, for example 20 mm.

Figure 6:
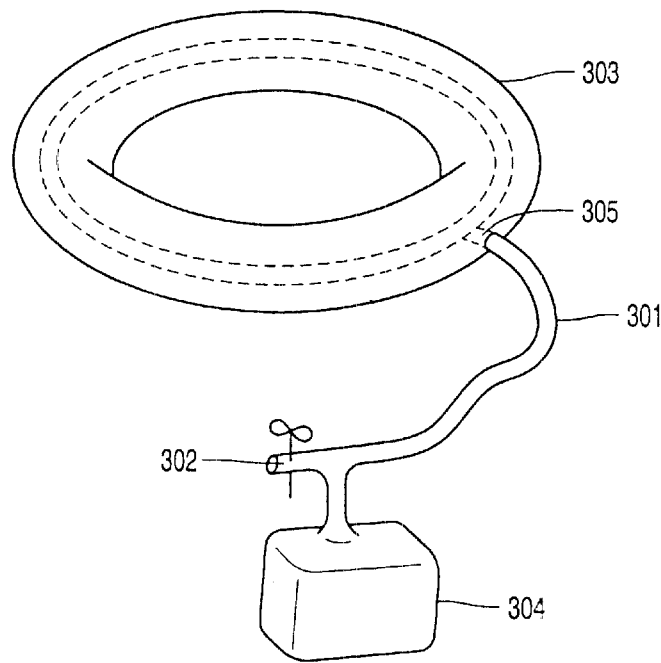
FIG. 6 shows a second embodiment of the sealing ring.

A second embodiment of the sealing ring according to the invention is made of a material which contains, for example latex or a silicon rubber. This second embodiment is preferably provided with an internal chamber. This chamber preferably extends along the circumference of the sealing ring. The chamber is capable of containing a quantity of gas or a mixture of gases, for example air. In order to adapt the elasticity of this embodiment of the sealing ring, the chamber can also be connected to a rigid pressure vessel. The volume of the pressure vessel is preferably much greater than the volume of the chamber. The elasticity of the sealing ring can in that case be adjusted by variation of the quantity of gas present in the sealing ring, so that the ring can be substantially completely compressed under the weight of the body to be examined. This embodiment of the sealing ring according to the invention will be described in detail hereinafter with reference to FIG. 6. FIG. 6 shows a second sealing ring 303, a tube 301, a valve 302, a pressure vessel 304 and a chamber 305. The chamber 305 in the second sealing ring 303 is connected to the pressure vessel 304 via the tube 301 and the valve 302. Via the valve 302, the overpressure in the chamber 305 in the second sealing ring 303 is adjusted to, for example approximately 100 hPa. As a result, the second sealing ring 303 has an elasticity such that it is substantially completely compressed under the weight of the body to be examined. The second embodiment 303 of the sealing ring is also arranged on the edge portion 204 of the holder 13, so that this sealing ring also seals the part 202 of the breast to be imaged and the matching liquid 201 in the holder 13. In order to simplify the replacement of the second embodiment of the sealing ring, it can also be provided with an adapter ring. For example, this adapter ring is of the type used for the first embodiment of the sealing ring. Instead of filling the internal chamber with air, it can also be filled with a liquid. The rigid pressure vessel should in that case be replaced by an expansion vessel.

In order to avoid artefacts in the reconstruction, furthermore, the inner side of the holder and the side of the two embodiments of the sealing rings 203, 303 which faces the holder may be provided with a diffuse reflector, for example by application of a lacquer containing titanium dioxide. The surface of the sealing ring outside the holder is preferably painted black, so that as little as possible ambient light can penetrate the measuring space within the holder.

A liquid pump can be used so as to replenish any matching liquid escaping from the holder. FIG. 1 shows a liquid pump 50 and a reservoir 52 for matching liquid. The inlet 53 of the liquid pump is connected to the reservoir 52 and an outlet 51 of the liquid pump is connected to the opening in the lower side of the holder 13. A flow of, for example 100 ml per minute suffices to replace the escaping matching liquid. It is a further advantage that any air bubbles trapped between the part of the breast to be imaged and the inner wall of the holder can then be filled up with the supplied matching liquid. Furthermore, the level of the matching liquid is raised in comparison with that in a known device without sealing ring. Such a raised level of the matching liquid will be elucidated with reference to FIG. 2. Raising the level of the liquid increases the distance between the surface 210 of the matching liquid 201 and the respective openings for the optical conductors 5, 9, 30, 35 connected to the selection unit 4 or the photodetectors 38, 45. This also counteracts artefacts in the reconstructed image.

All references cited herein, as well as the priority document European Patent Application 99200886.2 filed Mar. 23, 1999, are incorporated herein by reference in their entirety and for all purposes to the same extent as if each individual publication or patent or patent application was specifically and individually indicated to be incorporated by reference in its entirety for all purposes.

What is claimed is:

1. A device for imaging the interior of a turbid medium comprising:
   a holder which has only one open side bounded by an edge portion, completely encloses a measuring volume and is arranged to receive a matching liquid and the turbid medium,
   a light source for irradiating the turbid medium and the matching liquid, a photodetector for measuring a part of the intensities of light transported through the turbid medium and the matching liquid, a control unit for reconstructing an image of the interior of the turbid medium on the basis of the measured light intensities, and an elastically deformable sealing ring which is provided on the edge portion of the holder to seal a desired portion of the turbid medium and matching liquid within the holder and to maintain a maximum level of matching fluid in the holder during light imaging.

2. A device as claimed in claim 1, wherein the sealing ring further comprises polyurethane (PUR) of a density in a range of from 0.01 to 0.4 kg/l.

3. A device as claimed in claim 1, wherein the sealing ring further comprises an internal chamber which extends along at least a part of the circumference of the sealing ring.

4. A device as claimed in claim 3, wherein the internal chamber further comprises a gas.

5. A device as claimed in claim 4, wherein the internal chamber further comprises a connection to a rigid pressure vessel.

6. A device as claimed in claim 3, wherein the sealing ring is made of a material comprising latex or silicon.

7. A device as claimed in claim 1, further comprising a diffuse reflector provided on a side of the sealing ring which faces the measuring volume of the device.

8. A device as claimed in claim 1, wherein the sealing ring further comprises an adapter ring for attaching the sealing ring to the edge portion of the holder.

9. A device as claimed in claim 1 further comprising a reservoir for storing matching liquid, and a pump which is connected between the reservoir and the holder in order to adjust the level of the matching liquid to be received by the holder.

10. The elastically deformable sealing ring set forth in claim 1, wherein said sealing ring is provided on the edge portion of a holder for use in a device for imaging the interior of a turbid medium.

11. The elastically deformable sealing ring of claim 10 which is made of a material comprising polyurethane (PUR) of a density in a range of from 0.01 to 0.4 kg/l.

12. The elastically deformable sealing ring of claim 10 further comprising an internal chamber which extends along at least a part of the circumference of the sealing ring.

13. The elastically deformable sealing ring of claim 12 wherein the internal chamber further comprises a gas.

14. The elastically deformable sealing ring of claim 13 wherein the internal chamber further comprises a connection to a rigid pressure vessel.

15. The elastically deformable sealing ring of claim 12 which is made of a material comprising latex or silicon.

16. The elastically deformable sealing ring of claim 10 further comprising a diffuse reflector which is provided on a side of the sealing ring which faces the measuring volume of the device.

17. The elastically deformable sealing ring of claim 10 further comprising an adapter ring for attaching the sealing ring to the edge portion of the holder.

18. The elastically deformable sealing ring of claim 10 further comprising a reservoir for storing matching liquid, and a pump which is connected between the reservoir and the holder in order to adjust the level of the matching liquid to be received by the holder.

* * * * *